(12) United States Patent
Ohkouchi et al.

(10) Patent No.: US 7,005,544 B2
(45) Date of Patent: Feb. 28, 2006

(54) METHOD FOR PREVENTING POLYMERIZATION IN AN ACRYLIC ACID MANUFACTURING PROCESS

(75) Inventors: Kazuo Ohkouchi, Himeji (JP); Tomohiro Nakae, Himeji (JP); Kazuhiko Sakamoto, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 141 days.

(21) Appl. No.: 10/651,031

(22) Filed: Aug. 29, 2003

(65) Prior Publication Data

US 2004/0044120 A1 Mar. 4, 2004

(30) Foreign Application Priority Data

Sep. 3, 2002 (JP) .......................... 2002-258046

(51) Int. Cl.
*C07C 51/42* (2006.01)

(52) U.S. Cl. ...................... 562/600; 562/598; 562/532; 203/73; 203/80; 203/81

(58) Field of Classification Search ............... 203/73, 203/80, 87, 81; 562/600, 532, 598
See application file for complete search history.

(56) References Cited

U.S. PATENT DOCUMENTS

| 4,358,347 A | * | 11/1982 | Mettetal et al. ............... 203/38 |
| 5,322,960 A | | 6/1994 | Sakamoto et al. |
| 5,785,821 A | * | 7/1998 | Sakamoto et al. ............ 203/57 |

FOREIGN PATENT DOCUMENTS

| EP | 0 861 820 | | 9/1998 |
| EP | 861820 A2 | * | 9/1998 |
| EP | 1 298 120 | | 4/2003 |
| JP | 6-345681 | | 12/1994 |
| JP | 9-95465 | | 4/1997 |

* cited by examiner

*Primary Examiner*—David W. Wu
*Assistant Examiner*—Satya B. Sastri
(74) *Attorney, Agent, or Firm*—Wenderoth, Lind & Ponack, L.L.P.

(57) ABSTRACT

A method for effectively preventing polymerization of acrylic acid during an azeotropic dehydration distillation in an acrylic acid manufacturing process and thus enabling stable operation of the azeotropic dehydration column over an extended period of time. The acrylic acid is separated in an azeotropic dehydration column from an acrylic acid aqueous solution fed therein, and the method includes withdrawing from the bottom of the azeotropie dehydration column a bottom effluent containing 50% or more of glyoxal (including the hydrates thereof) contained in the acrylic acid aqueous solution fed into the azeotropic dehydration column.

6 Claims, 1 Drawing Sheet

METHOD FOR PREVENTING POLYMERIZATION IN AN ACRYLIC ACID MANUFACTURING PROCESS

BACKGROUND OF THE INVENTION

1. Field of the Invention

The present invention relates to a method for preventing polymerization of acrylic acid during distillation thereof, and more particularly to a method for preventing polymerization of acrylic acid, during azeotropic dehydration distillation of an acrylic acid aqueous solution in an acrylic acid production process, due to by-products present in the acrylic acid aqueous solution (feed liquid) and for preventing deposition of the by-products in the distillation column.

2. Description of the Prior Art

An enormously large amount of acrylic acid has been produced in large-scale manufacturing plants. A typical process of manufacturing the same is described below. First, propylene and/or acrolein (hereinafter, referred to as "propylene and the like") are brought into contact in a gas phase with a molecular oxygen-containing gas, and catalytically oxidized to give a reaction gas. The reaction gas contains, together with the desired product acrylic acid, various compounds including unreacted acrolein and by-products such as formaldehyde, glyoxal, furfural, benzaldehyde, formic acid, acetic acid, and maleic acid. Subsequently, the reaction gas was brought into contact with and absorbed in an absorption liquid, such as water, giving an acrylic acid aqueous solution, and the impurities such as the by-products and water contained in the acrylic acid aqueous solution were removed by means of distillation or the like to produce high purity acrylic acid. As there is not a sufficiently large difference in relative volatility between acrylic acid and water or between acrylic acid and acetic acid, it is difficult to have high-purity acrylic acid in a simple distillation process. Accordingly, an azeotropic distillation process, wherein a mixture of an acrylic acid aqueous solution and an azeotropic solvent is distilled together, is typically used as the distillation process. In addition, a temperature of the distillation needs to be increased for removing the impurities, which raises a problem that acrylic acid itself tends to polymerize during the distillation. Therefore, a variety of polymerization inhibitors are introduced into the distillation column for the purpose of preventing the polymerization of acrylic acid therein and ensuring a consistent operation of the distillation for an extended period of time.

As such processes are known: a process for preventing the polymerization of acrylic acid by introducing into the distillation column N-nitrosophenylhydroxyamine or the salt thereof along with a copper salt compound (see Japanese Unexamined Patent Publication No. 9-95465); and a process for preventing the polymerization of acrylic acid by introducing into the distillation column a three-component polymerization inhibitor consisting of an N-oxyl compound, a phenol compound, and a phenothiazine compound along with molecular oxygen (see Japanese Unexamined Patent Publication No. 6-345681).

A variety of other polymerization inhibitors along with those described above have been proposed as the means for preventing the polymerization of acrylic acid, but each of the polymerization inhibitors, although highly effective for prevention of polymerization of acrylic acid during storage, is not so dominant for preventing the polymerization of acrylic acid during distillation, especially during azeotropic dehydration distillation (herein after may be called as azeotropic dehydration). In addition, as described later, the present inventors have found that these polymerization inhibitors are not effective for prevention of deposition of by-products contained in the acrylic acid aqueous solution. For an commercial-scale production of acrylic acid, which requires operation over quite a long period of time, a polymerization inhibitor that retains an excellent potential for preventing the polymerization of acrylic acid for an extended period of time is desired, but there is no such inhibitors available yet that could satisfy the need.

An object of the present invention is to provide a method for effectively suppressing the polymerization of acrylic acid and the deposition of by-products during an azeotropic dehydration distillation in an acrylic acid manufacturing process and ensuring a consistent operation of the azeotropic dehydration distillation column over an extended period of time.

SUMMARY OF THE INVENTION

Figure 1:
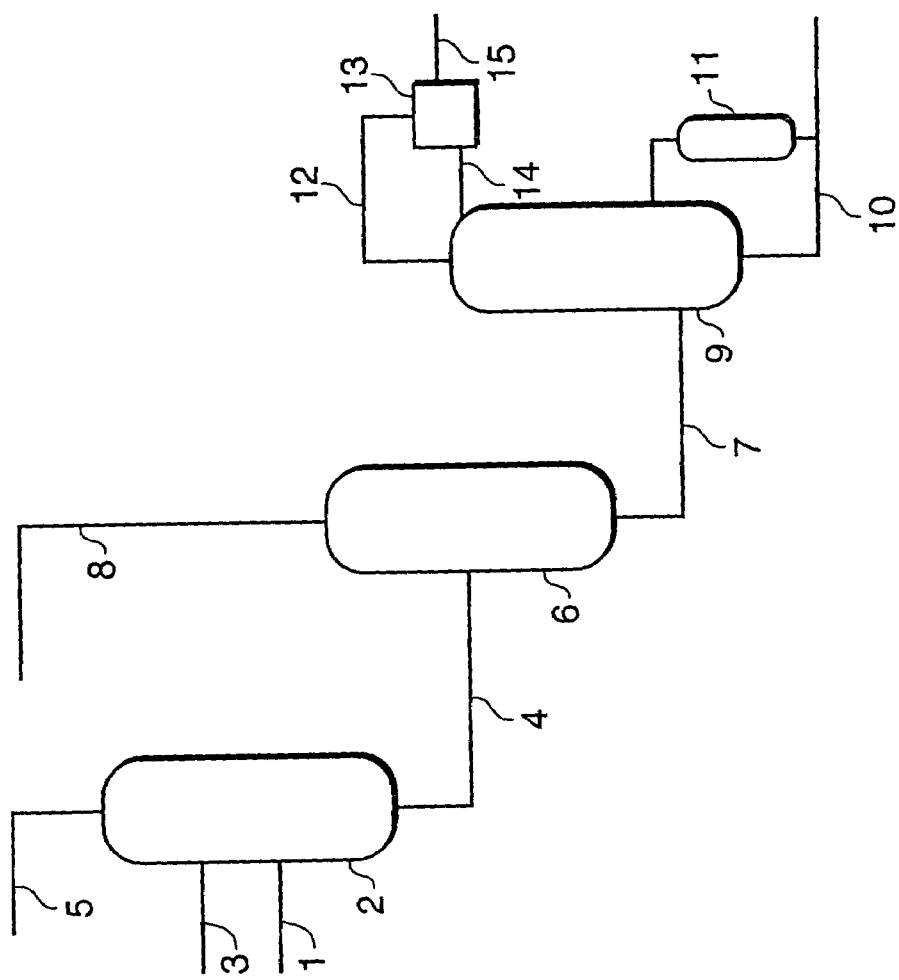
FIG. 1 shows a schematic flow chart of an acrylic acid manufacturing process.

A method for preventing polymerization of an acrylic acid during a separation of the acrylic acid from an acrylic acid aqueous solution comprising:
- the acrylic acid aqueous solution contains glyoxal and/or its hydrate;
- the separation is conducted in an azeotropic dehydration column in the presence of an azeotropic solvent;
- the acrylic acid and the glyoxal and/or its hydrates are separated from the acrylic acid aqueous solution and withdrawn from the bottom of the column, wherein;
- 50% or more of the glyoxal and/or its hydrate with respect to 100% of total glyoxal and/or its hydrate contained in the acrylic acid aqueous solution are withdrawn from the bottom of the column.

DETAILED DESCRIPTION OF PREFERRED EMBODIMENTS

In search of a completely new method for improvement in the inhibitory effect on the acrylic acid polymerization in the azeotropic dehydration distillation column (herein after may be called as azeotropic dehydration column), not just by improvement of the conventional polymerization inhibitor, after an intensive study of various problems occurring in the azeotropic dehydration column such as the acrylic acid polymerization and the deposit formation during distillation, the present inventors have found that the polymerization of acrylic acid in the column was mainly caused by two reasons: one reason is temperature in the column since acrylic acid is easily polymerized at high temperature. Another reason is impurities (especially glyoxal and its hydrates) contained in feed liquid (i.e. acrylic acid aqueous solution) since impurities induce the formation of polymerization materials or impurities itself are accumulated and deposited in the column. Furthermore, it was found that the conventional polymerization inhibitors are effective only for prevention of the acrylic acid polymerization due to the former reason (temperature related reason) and not sufficiently effective to the polymerization and deposition due to the latter reason (impurity related reason). In particular, glyoxal and/or its hydrate (herein after may be just called "glyoxal"), one of the impurities contained in the feed liquid, tends to accumulate in a azeotropic dehydration column under the conventional operating condition for azeotropic dehydration distillation and to condense over time, forming and depositing polymeric materials, which causes a deviation in flow of the gas or liquid stream passing through the column and an uneven distribution of the polymerization inhibitor within the column. As a result, various polymers are generated due to the glyoxal derivatives in the column, for example, by polymerization of acrylic acid or acceleration thereof due to the deposits, impeding a continuous consistent operation of the distillation column over an extended period of time under an ordinary operation condition. The present invention was completed based on these findings. According to the present invention, 50% or more, preferably 70% or more, more preferably 90% or more, still more preferably 95% or more of glyoxal contained in the acrylic acid aqueous solution is withdrawn from the bottom of an azeotropic dehydration column, ensuring an effective suppression of the accumulation of the glyoxal (in a variety of forms including polymers) in the column during distillation, and thus preventing the above adverse effects derived from the glyoxal and allowing a continuous operation for a period longer than that of the conventional process.

Hereinafter, the method of the present invention will be described with reference to the acrylic acid manufacturing process exemplified in FIG. 1, but the present invention is characterized in that 50% or more of glyoxal with respect to 100% of total glyoxal contained in the acrylic acid aqueous solution supplied into an azeotropic dehydration column is withdrawn from the bottom of the column. It should be understood that the description of the manufacturing process below is not intended to limit the scope of the present invention and that the manufacturing process may be modified if desired so far as the modifications do not interfere with the advantageous effect of the present invention.

In a favorable embodiment of the present invention, the concentration of water in the liquid phases at the 3rd to 6th plate of theoretical plates from the bottom of the azeotropic dehydration column is recommended to be 0.1 mass % or more. In another favorable embodiment, the concentration of acrylic acid in the aqueous phase of the condensate extracted from the top of the azeotropic dehydration column is set at 0.5 to 5.0 mass %; 30% or more of acetic acid contained in the feed liquid is withdrawn from the bottom of the azeotropic dehydration column; or a specific solvent is used as the azeotropic solvent.

A gas mixture obtained by a catalytic gas-phase oxidation of propylene and/or acrolein with a molecular oxygen-containing gas or the like under any condition is supplied via a line 1 into an absorption column 2. An absorption liquid is supplied via a line 3 into the absorption column 2, wherein the absorption liquid is brought into contact with the gas mixture and absorbs acrylic acid contained therein. The resulting acrylic acid aqueous solution that contains the absorbed acrylic acid is then fed via a line 4 to the next process. Remaining gas deprived of acrylic acid is discharged via a line 5 and sent to any other process, for example, back to the above catalytic gas-phase oxidation process or to a combustion process.

As described above, the acrylic acid aqueous solution contains, together with acrylic acid, acrolein remaining unreacted and by-products generated during the catalytic gas-phase oxidation, for example, formaldehyde, glyoxal, furfural, benzaldehyde, formic acid, acetic acid, and maleic acid as impurities.

The acrylic acid aqueous solution thus obtained may be sent, directly via a line 4 or indirectly via any steps according to specific needs, into an azeotropic dehydration column.

For the purpose of reducing the amount of acrolein remaining in the acrylic acid aqueous solution, a stripping tower 6, for example, may be additionally installed as shown in FIG. 1. The acrylic acid aqueous solution deprived of acrolein in the stripping tower 6 is then fed via a line 7 into the azeotropic dehydration column 9.

Meanwhile, acrolein vaporized in the stripping tower 6 may be sent via a line 8 to any process for disposal or reutilization. In the azeotropic dehydration column 9 of the present invention, water and acrylic acid contained in the acrylic acid aqueous solution are separated and extracted respectively from the top (water) and bottom (acrylic acid) of the column (dehydration distillation). As there is not a large difference in relative volatility between water and acrylic acid and thus the separation thereof is not easily achieved by a simple distillation method, acrylic acid is generally separated by an azeotropic distillation of a mixture of an acrylic acid aqueous solution and an additional azeotropic solvent, whereby a water-azeotropic solvent mixture is distilled from the top of the column. The separated acrylic acid (crude acrylic acid) is withdrawn from the bottom of the column.

From a viewpoint of facilitating separation and recovery of the azeotropic solvent in azeotropic solvent separation means 13, the azeotropic solvent is preferably substantially insoluble in water and more specifically has a solubility in water of preferably 0.5 mass % or less, more preferably 0.3 mass % or less at room temperature. In particular, the use of an azeotropic solvent having the solubility of 0.1 mass % or less is recommended as it can prevent migration of the solvent into the aqueous phase (i.e., loss of the solvent). On the other hand, the use of an azeotropic solvent having a water solubility of 0.5 mass % or more would necessitate installation of an additional process for separation and recovery of the azeotropic solvent contained in the aqueous phase of the condensate from the top of the column.

As the azeotropic solvent, the recommended azeotropic solvent is, for example, the solvent containing at least one selected from the group consisting of aliphatic hydrocarbons having 7 or 8 carbons such as heptane and aromatic hydrocarbons having 7 or 8 carbons such as toluene. With an azeotropic solvent having less than 7 carbons, the amount of water in the azeotrope is restricted, resulting in an increase in the quantity of heat required for the azeotropic dehydration distillation. Alternatively, with an azeotrope having more than 8 carbons, the boiling point of the azeotropic mixture become higher, making it more difficult to remove the azeotropic solvent along with water and resulting in an increase in the content of the azeotropic solvent contained in the bottom effluent. Favorable examples of the azeotropic solvent include toluene, xylene, heptane, and cyclohexane, and these solvents may be used alone or in combination of two or more solvents according to the purpose.

As the azeotropic dehydration column 9 may be used any kind of columns known in the art, such as plate columns and packed columns, so long as the azeotropic dehydration distillation can be conducted therein. In addition, the configuration of the azeotropic dehydration column 9 is also not particularly restricted, but preferably the column has 10 or more of theoretical plates. In the present invention, both the number of theoretical plates and actual plates are numbered from the bottom of the column. The upper limit of the number of theoretical plates is not particularly limited, but preferably not more than 30. The number of theoretical plates may be suitably selected from a range of 15 to 25 according to the design of the column.

Glyoxal tends to deposit when a water concentration decreases and thus to prevent the deposition of the glyoxal, the concentration of water in the liquid phases at 3rd to 6th plate of theoretical plates from the bottom of the column is preferably maintained at 0.1 mass % or more, more preferably 0.2 mass % or more, still more preferably 0.3 mass % or more, and preferably 5 mass % or less, more preferably 2 mass % or less, still more preferably 1 mass % or less. It is preferable to keep the concentration of water at the same theoretical plate number at not less than 0.1 mass %, as it enables withdrawal of glyoxal as the hydrate from the bottom of the column while preventing deposition of glyoxal in the column. On the other hand, for the purpose of decreasing the concentration of water in the crude acrylic acid to be withdrawn from the bottom of the column especially to as low as 1000 ppm or less, it is recommended to keep the water concentration at the same theoretical plate number at 5 mass % or less. From this viewpoint, the temperature at the 8th to 9th plate of theoretical plates (e.g., the 25th plate of the actual plate in a column having a total of 50 actual plates) is desirably, suitably controlled in such a manner that the concentration of water at the 3rd to 6th plate of theoretical plates is maintained in the above range.

Additionally, in order to withdraw 50% or more, more preferably 70% or more, more preferably 90% or more, still more preferably 95% or more of glyoxal from the bottom of the column, the temperature in the column (at 8th to 9th plate of theoretical plates) is desirably so controlled that the concentration of acrylic acid in the aqueous phase of the condensate from the top of the azeotropic dehydration column is maintained at preferably 0.5 mass % or more, more preferably 0.8 mass % or more, still more preferably 1 mass % or more. Even though the concentration of acrylic acid in the aqueous phase of the condensate may be increase by the above temperature adjustment, an excessive increase in the concentration of acrylic acid is often accompanied by the increase in the amount of polymerization within the column, and thus it is preferable to control the temperature so that the concentration of acrylic acid is maintained at preferably 5 mass % or less, more preferably 3 mass % or less, still more preferably 2 mass % or less.

During the control of acrylic acid concentration in the aqueous phase of the condensate, it is preferable to control the temperature suitably in the column (at 8th to 9th plate of theoretical plates) so that preferably 30% or more, more preferably 50% or more of acetic acid contained in the acrylic acid aqueous solution supplied into the column may be withdrawn from the bottom of the column. Even when the concentration of acrylic acid in the aqueous phase is in the range above, glyoxal may not be sufficiently withdrawn from the bottom of the column if the withdrawal rate of acetic acid in the bottom effluent is 30% or less.

In other words, the concentration of water, acrylic acid, and acetic acid can be suitably controlled by properly setting the operational condition as will be described below, but the temperature condition for the control of these concentration cannot be decided definitely and thus should be determined by taking into consideration various factors such as the property of the acrylic acid aqueous solution and the azeotropic solvent to be supplied into the azeotropic dehydration column, and the size of the column. Accordingly, it is preferable to properly control the operational condition by taking these factors into consideration so that the preferred concentration described above will be achieved.

The temperature at the top of the column is preferably maintained at preferably 40° C. or more, as the water concentration in the crude acrylic acid withdrawn from the bottom thereof becomes 1000 ppm or less at the temperature; but the temperature is also preferably kept at not higher than 50° C., as when the top temperature is raised to over 50° C., the concentration of acrylic acid contained in the condensate increases, resulting in a reduction in the yield of acrylic acid and occasionally in polymerization of acrylic acid at the top of the column.

Alternatively, the bottom temperature of the column is preferably controlled in a range of 90° C. to 110° C. The control of the bottom temperature in the range above is recommended as it prevents an increase in concentration of acrylic acid dimer in the bottom effluent and thus a reduction in yield of acrylic acid.

The bottom effluent withdrawn via a line 10 from the bottom of the azeotropic dehydration column 9 contains high-boiling temperature compounds such as polymerization inhibitors, acetic acid, and maleic acid as well as acrylic acid. Accordingly, in order to obtain highly purified acrylic acid by further purification, the crude acrylic acid may be purified if needed in any acrylic acid purification process known in the art, for example in an acetic acid separation column, high-boiling point material separation column, or rectification column, and thus the purification process of the crude acrylic acid is not particularly limited.

A polymerization inhibitor is supplied if desired for preventing the polymerization of the acrylic acid due to the temperature in the column, via any supplying means not shown in the figure. The polymerization inhibitor is a compound that has an inhibitory effect on polymerization of acrylic acid, and suitable examples of the polymerization inhibitor include hydroquinone, methoquinone, phenothiazine, copper dibutyldithiocarbamate, manganese acetate, 4-hydroxy-2,2,6,6-tetramethylpiperidinoxyl, 1,4-dihydroxy-2,2,6,6-tetramethylpiperidine, 4-hydroxy-2,2,6,6-tetramethylpiperidine, and nitrosophenol, and mixtures thereof. The amount of addition and the combination of these polymerization inhibitors are not particularly restricted and may be adjusted according to the operational condition, but, for example, in the case of an azeotropic dehydration column, the total amount of the polymerization inhibitors added is preferably 5 ppm or more, more preferably 50 ppm or more, still more preferably 100 ppm or more with respect to the total volume of vaporized acrylic acid, and preferably 2000 ppm or less, more preferably 1500 ppm or less, still more preferably 1000 ppm or less. The presence of the inhibitor at less than 5 ppm may not sufficiently inhibit the polymerization of acrylic acid in the azeotropic distillation column. On the other hand, the presence of the polymerization inhibitor at a concentration of more than 2000 ppm may raise a concern about coloring of the product, acrylic acid or the like.

Here, the total volume of vaporized acrylic acid means a total amount of the monomer gas evaporated at the bottom of the column in proportion to the heat supplied to the azeotropic dehydration column from heating means 11, such as reboiler, disposed to the azeotropic dehydration column 9 for recirculating part of the bottom effluent into the column and for keeping and raising the temperature inside the column.

The method for supplying the polymerization inhibitor is not restricted; for example, the inhibitor may be supplied as pre-mixed in a liquid to be supplied into the column, such as the acrylic acid aqueous solution or the reflux, or the polymerization inhibitor (herein, the polymerization inhibitor may be in any state: powder, liquid or gas) may be supplied directly, without any pre-mixing, into any portion, top or middle, of the distillation column. In addition, molecular oxygen, for example, may be supplied as the polymerization inhibitor into the column. Molecular oxygen may be supplied directly into the acrylic acid stream for example by air bubbling, or indirectly as pre-dissolved in a suitable other solvent. A method to supply molecular oxygen in a gas state into the bottom of the distillation column and/or the reboiler is particularly recommended, as such an oxygen supplying means, for example an air bubbling device, can be easily installed. Molecular oxygen is preferably added at an amount of about 0.1 to 1.0 vol. % with respect to the total volume of vaporized acrylic acid for achieving a desirable inhibitory effect on polymerization.

In the azeotropic dehydration column of the present invention, a mixture of water, an azeotropic solvent, and other are extracted in a gas phase (vaporized gas) from the top of the column. The vaporized gas is preferably condensed, by cooling means, such as a condenser, disposed in a line 12 (not shown in the figure) or not by condensing means, into a liquid phase (distillate), which is then fed into azeotropic solvent separation means 13. The distillate is allowed to separate therein to an organic phase (azeotropic solvent) and an aqueous phase (absorption liquid), and the azeotropic solvent separated in the azeotropic solvent separation means 13 is preferably refluxed via a line 14 into the azeotropic dehydration column 9, while at the same time the aqueous phase, to any step via a line 15. The aqueous phase containing acrylic acid may be treated in any manner and the treatment method is not particularly limited.

The reflux ratio (total mole number of the reflux per unit time/total mole number of the distillate per unit time) is not particularly limited, but is preferably adjusted in a range of 1.0 to 1.4, more preferably 1.0 to 1.2, as it enables to keep the water concentration of the liquid phases at the 3rd to 6th plate of theoretical plates in a favorable range. With a ref lux ratio of less than 1.0, the acrylic acid concentration in the aqueous phase of the condensate may increase, raising a possibility of polymerization of acrylic acid in the column, while with a reflux ratio of more than 1.4, the water concentration in the liquid phase at the 3rd to 6th plate of theoretical plates may decrease drastically, leading to an occasional difficulty in withdrawing glyoxal sufficiently from the bottom of the column.

Hereinafter, the present invention will be described in more detail with reference to EXAMPLES, but these EXAMPLES are not intended to limit the scope of the present invention.

EXAMPLE

Example 1

The following experiments are conducted according to the acrylic acid manufacturing process shown in FIG. 1. Propylene and a molecular oxygen-containing gas were supplied into a catalytic gas-phase oxidation reactor (having an internal tubular plate dividing the reactor into two, upper and lower, chambers) not shown in the figure, and subjected to catalytic gas-phase oxidation to give an acrylic acid-containing gas, which was fed via a line 1 into an absorption column 2. Acrylic acid was brought into contact with an absorption liquid (water) fed via a line 3 into the absorption column 2, giving an acrylic acid aqueous solution. The acrylic acid aqueous solution thus obtained contained as by-products acrolein, formaldehyde, furfural, glyoxal, acetic acid, formic acid and others. The acrylic acid aqueous solution was then fed via a line 4 into a stripping tower 6, wherein acrolein in the solution was stripped, giving an acrylic acid aqueous solution containing 30 mass % of water, 3.0 mass % of acetic acid, and 0.02 mass % of glyoxal. The acrylic acid aqueous solution was then supplied via a line 7 into an azeotropic dehydration column 9. The column 9 has an internal diameter of 105 mm and 50 stainless sieve trays (equivalent to $17^{th}$ plate of theoretical plates), a distance between the adjacent two trays being 147 mm, and equipped with a distillate pipe and a reflux feed pipe at the top of the column 9, a raw solution feed pipe and a polymerization inhibitor inlet pipe at the central portion (at the 28th tray from the bottom) of the column 9, and a bottom effluent outlet pipe and an oxygen inlet pipe at the bottom of the column 9. The acrylic acid aqueous solution was distilled using toluene (solubility in water: 0.05 mass % (25° C.)) as the azeotropic solvent. The amounts of polymerization inhibitors added were 10 ppm of copper dibutyldithiocarbamate, 100 ppm of hydroquinone, and 100 ppm of methoquinone with respect to the volume of the vaporized acrylic acid gas, and copper dibutyldithiocarbamate and methoquinone were supplied as dissolved in the ref lux into the top of the column 9, while the other polymerization inhibitor as dissolved in the acrylic acid aqueous solution into the central portion of the column 9. Additionally, molecular oxygen was supplied from the bottom of the column 9 in an amount of 0.3 vol. % with respect to the volume of the vaporized acrylic acid gas. Here, the volume of vaporized acrylic acid gas was the total amount of a monomeric acrylic acid gas to be vaporized from the bottom of the column 9, calculated from the amount of heat provided into the column 9 by the heating means such as a reboiler 11 (heating means for heating and recirculating at least part of the bottom effluent into the column 9 and for keeping or increasing the internal temperature thereof) disposed to the column 9.

Under a normal condition for steady operation, the top temperature of the azeotropic dehydration column 9 was adjusted to 45° C.; the bottom temperature thereof to 99° C.; the temperature at the 25th tray from the bottom thereof to 72° C.; the top pressure of the column 9 was adjusted to 150 hPa; the feed rate of the acrylic acid aqueous solution was 8.5 liter/hr; and the ref lux ratio of the distillate (total number of moles of the reflux per unit period/that of the distillate) was 1.1. Additionally, the water concentration of the liquid phases at the 3rd to $6^{th}$ plate of theoretical plates in the column 9 was kept at 0.3 mass % or more.

The condensate from the top of the column 9 was fed into a reservoir (azeotropic solvent separation means) 13, wherein the azeotropic solvent and the absorption liquid were separated respectively as organic and aqueous phases. The aqueous phase contained 2.6 mass % of acetic acid, 1.7 mass % of acrylic acid, 0.0005 mass % of glyoxal, 1.7 mass % of formaldehyde, 0.6 mass % of formic acid, and 0.02 mass % of acrolein. On the other hand, the bottom effluent withdrawn from the bottom of the column 9 contained 95.2 mass % of acrylic acid, 2.9 mass % of acetic acid (68% of that contained in the feed liquid), 0.02 mass % of water, 0.029 mass % of glyoxal, and 1.88 mass % of others. The bottom effluent contained no detectable amount of toluene (1 ppm or less), but almost all (99%) of glyoxal contained in the acrylic acid aqueous solution that was supplied via the line 7 into the column 9. The bottom effluent was further sent to and purified in an acetic acid separation column and a rectification column, giving high purity acrylic acid.

During a continuous production of acrylic acid for 30 days under the above condition, the column 9 was operated always in a stable and consistent manner. In addition, inspection of the interior of the column 9 after the operation was discontinued revealed no accumulation or deposition of glyoxal (including the polymers thereof) or acrylic acid-derived polymers.

Comparative Example 1

An azeotropic distillation of an acrylic acid aqueous solution was conducted in a similar manner to EXAMPLE 1, except that the reflux ratio of the azeotropic dehydration column was 1.5; the concentration of acetic acid in the bottom effluent withdrawn from the bottom of the column 9, 1.8 mass %; that of toluene, 13.4 mass %: that of others, 1.90 mass %; and the water concentration at the $3^{rd}$ to $6^{th}$ plate of theoretical plates of the column 9, 0.05 mass % or less.

The aqueous phase of the condensate from the top of the column 9 contained acetic acid at 5.7 mass %, acrylic acid at 0.2 mass %, and glyoxal at 0.03 mass %. Alternatively, the bottom effluent obtained from the bottom contained acetic acid at 1.8 mass % (42% of that contained in the feed liquid), toluene at 13.4 mass %, and others at 1.90 mass %, and there was no glyoxal found in the bottom effluent.

A continuous operation of the column 9 was conducted under the same condition. The azeotropic distillation was stable for some time after the beginning of the operation, but pressure drop in the column gradually increased from the 10th day of operation and reached on the 12th day to such a large value that the azeotropic distillation cannot be continued any more. Disassembly and inspection of the column 9 after 12 days of operation revealed the accumulation and deposition of a great amount of glyoxal (including the polymers) in the column 9.

Comparative Example 2

An azeotropic distillation of an acrylic acid aqueous solution was conducted in a similar manner to EXAMPLE 1 except that the temperature at the 25th tray from the bottom of the azeotropic dehydration column 9 was set at 67° C. and the water concentration of the liquid phases at $3^{rd}$ to $6^{th}$ plate of theoretical plates in the column 9 was adjusted at 0.08 mass %.

The aqueous phase of the condensate from the top of the column 9 contained acetic acid at 6.9 mass %, acrylic acid at 0.6 mass %, and glyoxal at 0.02 mass %. On the other hand, the bottom effluent withdrawn from the bottom of the column 9 contained acetic acid at 0.8 mass % (19% of that contained in the feed liquid), glyoxal at 0.011 mass %, and toluene at 0.0001 mass %. The bottom effluent contained 39% of glyoxal contained in the acrylic acid aqueous solution supplied via the line 7. A continuous production of acrylic acid was conducted under this condition. While the azeotropic distillation was stable for some time from the beginning of the operation, pressure drop in the column 9 gradually increased after 25 days of operation, and reached to such a large value on the 26th day that the azeotropic distillation could not be continued any more. Disassembly and inspection of the column 9 after the operation was discontinued on the 26th day revealed accumulation and deposition of a great amount of glyoxal (including the polymers).

Example 2

An azeotropic distillation of an acrylic acid aqueous solution was conducted in a similar manner to EXAMPLE 1, except that the temperature of the 25th tray from the bottom of the azeotropic dehydration column 9 was set at 70° C. and the water concentration of the liquid phases at the $3^{rd}$ to $6^{th}$ plate of theoretical plates in the column 9 was adjusted at 0.2 mass %.

The aqueous phase of the condensate from the top of the column 9 contained acetic acid at 7.2 mass %, acrylic acid at 0.7 mass %, and glyoxal at 0.024 mass %. Alternatively, the bottom effluent withdrawn from the bottom of the column 9 contained acetic acid at 0.7 mass % (16% of the contained in the feed liquid), glyoxal at 0.016 mass %, and toluene 0.0001 mass %. The bottom effluent contained 57% of glyoxal contained in the acrylic acid aqueous solution supplied via the line 7. During a continuous production of acrylic acid under this condition, there was observed a slight pressure drop in the column 9 but it was still possible to operate continuously for 30 days. Disassembly and inspection of the column 9 after the operation was discontinued revealed accumulation and deposition of a small amount of glyoxal (including the polymers).

Example 3

An azeotropic distillation of an acrylic acid aqueous solution was conducted in a similar manner to EXAMPLE 1, except that the reflux ratio of the azeotropic dehydration column 9 was set at 1.06, the temperature of the 24th tray from the bottom of the column was at 65° C., and the water concentration of the liquid phase at the 3rd to 6th plate of theoretical plates in the column 9 was adjusted at 0.25 mass %.

The aqueous phase of the condensate from the top of the column 9 contained acetic acid at 5.7 mass %, acrylic acid at 0.9 mass %, and glyoxal at 0.028 mass %. Alternatively, the bottom effluent withdrawn from the bottom of the column 9 contained acetic acid at 1.6 mass % (37% of that contained in the feed liquid), glyoxal at 0.025 mass %, and toluene at 0.0001 mass %. The bottom effluent contained 86% of glyoxal contained in the acrylic acid aqueous solution supplied via the line 7. During a continuous production of acrylic acid under this condition, it was possible to operate continuously for 30 days. Disassembly and inspection of the column 9 after the operation was discontinued revealed accumulation and deposition of a very small amount (which means the amount is less than that of comparative examples) of glyoxal (including the polymers).

Comparative Example 3

An azeotropic distillation of an acrylic acid aqueous solution was conducted in a similar manner to EXAMPLE 1, except that the reflux ratio of the azeotropic dehydration column 9 was set at 0.96, the temperature of the 25th tray from the bottom of the column 9 was at 65° C., and the water concentration of the liquid phase at the $3^{rd}$ to $6^{th}$ plate of theoretical plates in the column 9 was adjusted at 0.35 mass %.

The aqueous phase of the condensate from the top of the column 9 contained acetic acid at 7.3 mass %, acrylic acid at 5.9 mass %, and glyoxal at 0.0004 mass %. Alternatively, the bottom effluent withdrawn from the bottom of the column 9 contained acetic acid at 0.7 mass % (16% of that contained in the feed liquid), toluene at 0.0002 mass %, and others at 2.0 mass %. A continuous production of acrylic acid was conducted under this condition. While the azeotropic distillation was conducted stably for some time from the beginning of the operation, pressure drop in the column 9 gradually increased after 7 days of operation and reached to such a large value on the 8th day that the azeotropic distillation could not be continued any more. Disassembly and inspection of the column 9 after the operation was discontinued on the 8th day revealed generation of a great amount of acrylic acid polymers. Under the condition where the aqueous phase of the condensate contains acrylic acid at more than 5 mass %, acrylic acid tends to polymerize in the column 9.

According to the present invention, withdrawal of 50% or more of glyoxal contained in the feed liquid to be supplied into an azeotropic dehydration column as contained in a bottom effluent enables suppression of accumulation and deposition of glyoxal (including the polymers thereof) in the column, thus preventing polymerization due to the glyoxal and ensuring a stable operation of the azeotropic distillation for an extended period of time.

In addition, an operation of the azeotropic dehydration column under the condition described above enables easy removal of 50% or more of glyoxal contained in the feed liquid from the bottom of the column, and thus prevents the accumulation of the glyoxal in the column. Further, an operation thereof under the more preferred operational condition described above is more favorable as it raises the withdrawal rate of the glyoxal. The withdrawal rate of glyoxal needed for achieving a stable operation over an extended period of time is 50% or more with respect to glyoxal contained in the feed liquid, but the withdrawal rate is favorably higher, preferably 70% or more, more preferably 90% or more, still more preferably 95% or more. According to the present invention, the withdrawal of 50% or more of the glyoxal prevents: accumulation of glyoxal as the hydrates thereof; as a result of the prevention of the glyoxal hydrates, precipitation of the glyoxal polymers, which are generated by condensation and heating of the glyoxal in the column; accordingly the troubles associated with clogging of the column; and polymerization of acrylic acid due to the glyoxal; thus enabling a stable operation of the azeotropic dehydration column over an extended period of time.

This application is based on Japanese patent application No. 2002-258046, filed in Japan Patent Office on Sep. 3, 2002, the contents of which are hereby incorporated by reference. Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for preventing polymerization of acrylic acid during separation of the acrylic acid from an acrylic acid aqueous solution containing glyoxal and/or its hydrate in an azeotropic dehydration column in the presence of an azeotropic solvent, wherein the method comprises withdrawing givoxal and/or its hydrate from the bottom of the column in an amount of 50% or more of the glyoxal and/or its hydrate with respect to 100% of total glyoxal and/or its hydrate contained in the acrylic acid aqueous solution.

2. The method according to claim 1, wherein the concentration of water in liquid phases at the $3^{rd}$ to $6^{th}$ theoretical plates in said azeotropic dehydration column is 0.1 mass % or more.

3. The method according to claim 1, wherein the concentration of acrylic acid in an aqueous phase of condensate from the top of said azeotropic dehydration column is 0.5 to 5.0 mass % and a bottom effluent withdrawn from the bottom thereof contains 30% or more of acetic acid contained in the acrylic acid aqueous solution fed into said azeotropic dehydration column.

4. The method according to claim 1, wherein said azeotropic solvent has a solubility in water of 0.5 mass % or less at room temperature.

5. The method according to claim 4, wherein said azeotropic solvent is an aliphatic hydrocarbon having a carbon number of 7 or 8 or an aromatic hydrocarbon having a carbon number of 7 or 8.

6. The method according to claim 1, wherein the temperature at the top of said azeotropic dehydration colunm is 40 to 5° C. and the temperature at the bottom thereof is 90 to 110° C.

* * * * *